(12) United States Patent
Sampson et al.

(10) Patent No.: US 9,803,047 B2
(45) Date of Patent: Oct. 31, 2017

(54) ALTERNATING RING-OPENING METATHESIS POLYMERIZATION

(71) Applicant: The Research Foundation for The State University of New York, Albany, NY (US)

(72) Inventors: Nicole S. Sampson, Setauket, NY (US); Li Tan, Centereach, NY (US); Kathlyn Parker, Centereach, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 15/438,305

(22) Filed: Feb. 21, 2017

(65) Prior Publication Data

US 2017/0158808 A1 Jun. 8, 2017

Related U.S. Application Data

(62) Division of application No. 14/906,834, filed as application No. PCT/US2014/047674 on Jul. 22, 2014, now Pat. No. 9,624,338.

(60) Provisional application No. 61/858,811, filed on Jul. 26, 2013, provisional application No. 61/857,189, filed on Jul. 22, 2013.

(51) Int. Cl.
*C08G 61/08* (2006.01)
*C09D 165/00* (2006.01)
*A61K 9/107* (2006.01)
*C09D 5/16* (2006.01)
*A61K 31/74* (2006.01)
*C08F 232/04* (2006.01)
*A61K 47/32* (2006.01)
*A61K 47/48* (2006.01)
*C08G 61/12* (2006.01)

(52) U.S. Cl.
CPC .......... *C08G 61/08* (2013.01); *A61K 9/1075* (2013.01); *A61K 31/74* (2013.01); *A61K 47/32* (2013.01); *A61K 47/48176* (2013.01); *A61K 47/48192* (2013.01); *C08F 232/04* (2013.01); *C08G 61/128* (2013.01); *C09D 5/1637* (2013.01); *C09D 165/00* (2013.01); *C08G 61/12* (2013.01); *C08G 2261/124* (2013.01); *C08G 2261/126* (2013.01); *C08G 2261/143* (2013.01); *C08G 2261/145* (2013.01); *C08G 2261/146* (2013.01); *C08G 2261/148* (2013.01); *C08G 2261/149* (2013.01); *C08G 2261/1424* (2013.01); *C08G 2261/1426* (2013.01); *C08G 2261/1428* (2013.01); *C08G 2261/1432* (2013.01); *C08G 2261/226* (2013.01); *C08G 2261/228* (2013.01); *C08G 2261/418* (2013.01); *C08G 2261/74* (2013.01)

(58) Field of Classification Search
CPC ..................... A61K 47/48176; C08G 61/08
See application file for complete search history.

(56) References Cited

U.S. PATENT DOCUMENTS

2011/0212046 A1* 9/2011 Sampson ......... A61K 47/48176
424/78.08

* cited by examiner

*Primary Examiner* — Jianfeng Song
(74) *Attorney, Agent, or Firm* — Fox Rothschild, LLP

(57) ABSTRACT

The invention relates to the field of polymers and olefin polymerization, and more specifically olefin metathesis polymerization. The invention provides regioregular alternating polymers and methods of synthesizing such polymers. To demonstrate, polymers were synthesized and modified with a FRET pair (Trp/Dansyl) post-polymerization.

7 Claims, 11 Drawing Sheets a)

b)

a)

b)

c)

ALTERNATING RING-OPENING METATHESIS POLYMERIZATION

CROSS REFERENCE TO RELATED APPLICATIONS

This application is a divisional of U.S. application Ser. No. 14/906,834, filed Jan. 21, 2016, which is a 371 of International patent application number PCT/US2014/047674 filed Jul. 22, 2014; which claims the benefit of priority to U.S. Application No. 61/857,189, filed Jul. 22, 2013, and U.S. Application No. 61/858,811, filed Jul. 26, 2013, which are incorporated herein by reference in their entireties.

STATEMENT OF INTEREST

This invention was made with government support under grant numbers HD038519 and GM097971 awarded by the National Institutes of Health and grant number DBI1039771 awarded by the National Science Foundation. The government has certain rights in the invention.

FIELD OF THE INVENTION

The invention relates to the field of polymers and olefin polymerization, and more specifically olefin metathesis polymerization.

BACKGROUND

Copolymers are employed in a wide range of materials, ranging from bulk plastics to specialized coatings, pharmaceutical compositions, and biomedical and electronic devices. Among the most commonly used are block copolymers, which often rely on phase separation of the two blocks for their functional properties, for example in drug delivery nanoparticles, and random copolymers, which incorporate two or more functional moieties that act co-operatively, for example in organic light emitting diodes. Regularly alternating polymers allow for controlled positioning of functional substituents, but they are difficult to access synthetically.

Regioregular alternating polymers (for example, SAN, styrene-acrylonitrile, an alternating copolymer used in plastics) are generally synthesized by radical polymerization with kinetic control of alternation in the polymerization reaction.[1,2] Recently, ring opening metathesis polymerization (ROMP) and ring opening insertion metathesis polymerization (ROIMP)[3] have been employed to synthesize alternating polymers: Ilker, M. F.; Coughlin, E. B. *Macromolecules* 2002, 35, 54-58; Choi, T. L.; Rutenberg, I. M.; Grubbs, R. H. *Angewandte Chemie-Intl. Ed.*, 2002, 41, 3839-3841; PCT publication WO 03/070779.

The existing methods of formation of alternating polymers are limited, and there remains a need for new and more structurally diverse substrates and polymers. The present invention provides substrate and catalyst combinations that can generate a wider range of alternating polymers, having a range of diverse properties.

Herein we address both, the limitation of the NB/COE ROMP, i.e. the formation of COE homoblocks, as well as the intramolecular chain transfer of current AROMP by utilizing CBE/CH monomers containing the DAN-PDI pair to achieve perfectly alternating copolymers. We show that these polymers exhibit a higher intensity charge-transfer absorbance than analogous poly(NB-alt-COE) polymers.

BRIEF DESCRIPTION OF THE INVENTION

The invention provides a method for producing an alternating AB copolymer comprising the repeating unit Ia, Ib, or Ic:

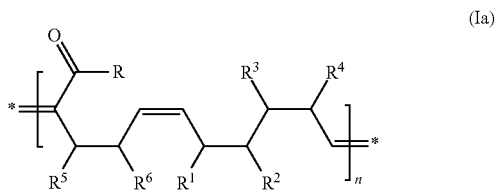

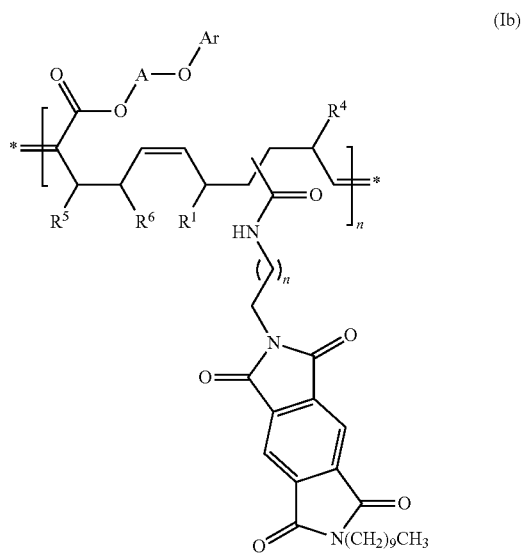

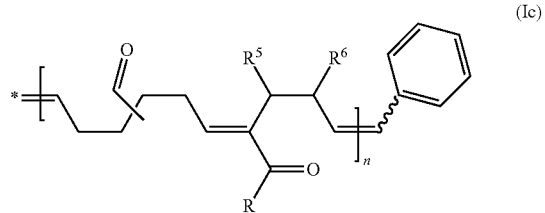

in which the A monomer is derived from a cyclobutene 1-carboxyl or 1-carbonyl derivative III, and the B monomer is derived from a cyclohexene derivative II.

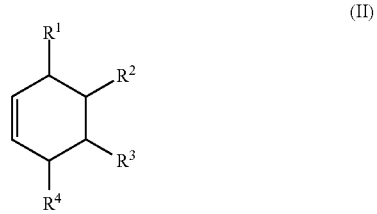

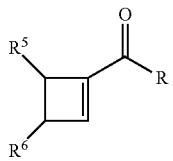

(III)

The method comprises contacting the cyclohexene derivative II with the cyclobutene derivative III in the presence of an olefin metathesis catalyst. This polymerization method enables the facile preparation of amphiphilic and bifunctional alternating polymers from simple and readily available starting materials.

DETAILED DESCRIPTION OF THE INVENTION

Figure 1:
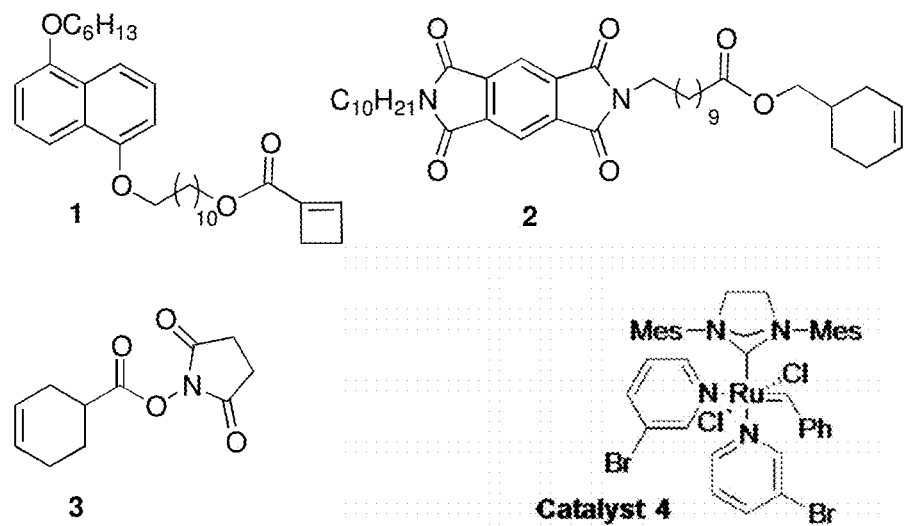
FIG. 1 shows chemical structures of monomers and catalyst (box) used for AROMP.

The invention provides a method for producing an alternating AB copolymer comprising the repeating unit Ia, Ib or Ic:

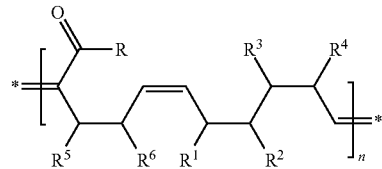

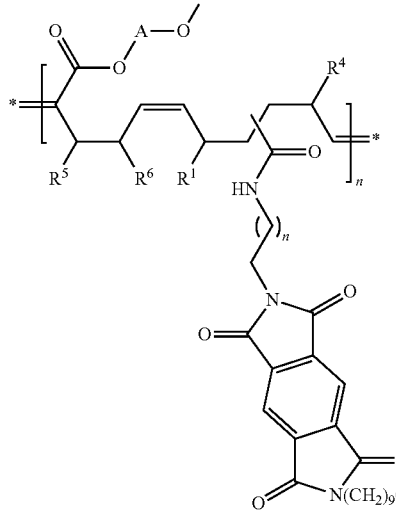

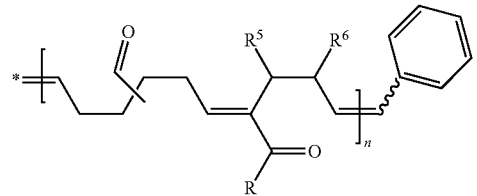

which comprises contacting an olefin of structure II with a cyclobutene of structure III

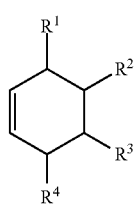

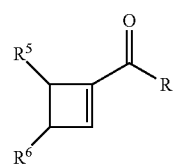

in the presence of an olefin metathesis catalyst. It will be understood that asterisk (*) at the end of a repeating unit can be interpreted as the point of attachment and may be terminated with a functional group as is known in the art. In the above structures, R may be, but is not limited to, H, $C_1$-$C_{20}$ alkyl, $C_2$-$C_{20}$ alkenyl, $C_3$-$C_8$ cycloalkyl, heterocyclyl, aryl, $C_1$-$C_{20}$ alkoxy, $C_1$-$C_{20}$ alkenyloxy, $C_3$-$C_6$ cycloalkyloxy, aryloxy, heterocyclyloxy, $C_1$-$C_{20}$ alkylamino, $C_1$-$C_{20}$ alkenylamino, $C_3$-$C_8$ cycloalkylamino, heterocyclylamino, or arylamino and may be optionally substituted with up to three substituents selected from halo, CN, $NO_2$, oxo, alkyl, cycloalkyl, alkenyl, alkynyl, aralkyl, aryl, and a heterocyclic group. In certain embodiments, the repeating unit, n, is between 2 and 20. Each substituent $R^1$ through $R^6$ may independently be, but is not limited to, H, aldehyde, $C_1$-$C_{20}$ alkyl, $C_2$-$C_{20}$ alkenyl, $C_3$-$C_6$ cycloalkyl, aryl, heterocyclyl, $C_1$-$C_{20}$ alkoxy, $C_1$-$C_{20}$ acyloxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, arylamino, or halogen; with the proviso that any carbon-carbon double bonds in R or in $R^1$ through $R^6$ are essentially unreactive toward metathesis reactions with the catalyst. It will be also understood that adjacent substitutions of $R^1$-$R^6$ may be taken together to form a 5- to 7-membered ring which may be optionally substituted with up to three substituents selected from halo, CN, $NO_2$, oxo, alkyl, cycloalkyl, alkenyl, alkynyl, aralkyl, aryl, and a heterocyclic group. In certain embodiments, A may be, but is not limited to $C_2$-$C_{20}$ alkyl. In another embodiment, A is $C_8$-$C_{12}$ alkyl. In another embodiment, $R^1$ through $R^6$ may be independently be C(O)NH—$C_1$-$C_{20}$ alkyl-N($R^7$)($R^8$). Each $R^7$ and $R^8$ are independently selected from H, $C_2$-$C_6$ alkyl, cycloalkyl, cycloalkenyl, alkyl-O-alkyl, alkyl-O-aryl, alkenyl, alkynyl, aralkyl, aryl and a heterocyclic group; or $R^7$ and $R^8$ may be taken together with the nitrogen to which they are attached form a 5- to 7-membered ring which may optionally contain a further heteroatom and may be optionally substituted with up to three substituents selected from halo, CN, $NO_2$, oxo, alkyl, cycloalkyl, alkenyl, alkynyl, aralkyl, aryl, and a heterocyclic group.

By way of example, suitable cyclohexene and cyclobutene species include but are not limited to the following:

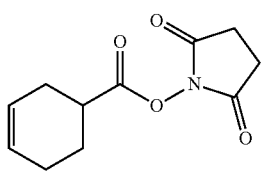

IIa

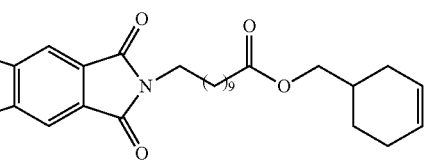

IIb

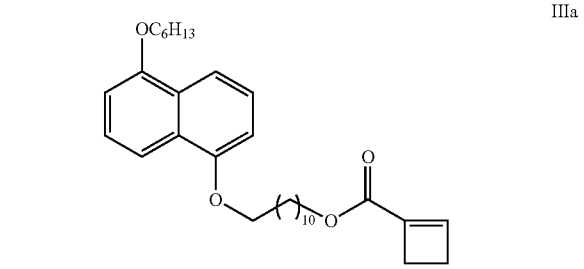

IIIa

It will be understood that olefins in the substituents should be essentially unreactive with the metathesis catalyst under the reaction conditions, so that the metathesis polymerization involves the cyclobutene and cyclohexene double bonds exclusively, or nearly so. Generally, any carbon-carbon double bonds in R or in $R^1$ through $R^6$ should be trisubstituted or tetrasubstituted, or otherwise rendered unreactive with the catalyst.

Aryl, as used herein, includes but is not limited to optionally substituted phenyl, naphthyl, anthracenyl, and phenanthryl groups. Heterocycle and heterocyclyl refer to monocyclic and fused polycyclic heteroaromatic and heteroaliphatic ring systems containing at least one N, O, S, or P atom. Aryl and heterocyclic groups may contain from 1 to 60 carbon atoms, and may range from furan, thiophene, and benzene to large chromophores such as phthalocyanines and fullerenes. For some applications, aryl and heterocyclic groups will preferably contain from 1 to 20 carbon atoms.

It will be apparent that alkyl, alkenyl, cycloalkyl, heterocyclyl, acyl, and aryl moieties in the substituents R and $R^1$ through $R^6$ may be substituted with functional groups known to be compatible with the catalyst. Examples include, but are not limited to, $C_1$-$C_4$ acyl, acyloxy, acylamino, amido, aryloxy, alkoxy and alkylthio groups; halogens; protected amino groups such as BocNH— and FmocNH—; protected hydroxy groups such as TMSO—, BzO—, and BnO—; and protected carboxyl groups such as —$CO_2$-t-Bu and —$CO_2$Bn. Accordingly, the terms alkyl, alkenyl, cycloalkyl, acyl, aryl, and heterocyclyl as used herein encompass such substituents.

The method may be used to prepare block copolymers as well, in which one block comprises the repeating units Ia, Ib, or Ic; the proportion of alternating and block copolymer regions in the polymer being dependent upon the catalyst and substrate. The catalyst may be any olefin metathesis catalyst known in the art, such as those disclosed in WO 03/070779. It is preferably an alkylidene ruthenium complex, and more preferably a complex of formula $(L)_2(L')X_2Ru=CHR'$, wherein R' may be, for example, H, $C_1$-$C_{10}$ alkyl, $C_2$-$C_{10}$ alkenyl, $C_3$-$C_6$ cycloalkyl, or aryl. The ligand L is typically a trialkyl phosphines, triarylphosphines, tri(cycloalkyl)phosphines, pyridines, aryl, wherein aryl is optionally substituted with a halogen. L' is a second ligand, and may be a trialkyl phosphine, triarylphosphine, tri(cycloalkyl)phosphine, or a pyridine. L' may also be an imidazolin-2-ylidine carbene of formula IV:

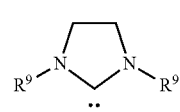

IV wherein $R^9$ may be selected from the group, but is not limited to a $C_1$-$C_6$ alkyl group or aryl. In certain embodiments, X is a halogen or pseudohalogen such as F, Cl, Br, $NO_3$, $CF_3$, or $CF_3COO^-$.

In certain embodiments, L is a pyridine, optionally 3-bromopyridine; and L' is an imidazolin-2-ylidine carbene. In another embodiment, $R^9$ is preferably mesityl, 2-methylphenyl, 2-ethylphenyl, 2-isopropylphenyl, 2,3-diisopropylphenyl, 2, 6-difluorophenyl, or 3,5-di-t-butylphenyl.

The invention also provides the following polymer comprising the repeating unit Ia, Ib, or Ic.

The polymers of the present invention may be prepared according to the representative Schemes 1 through 3.

Scheme 1
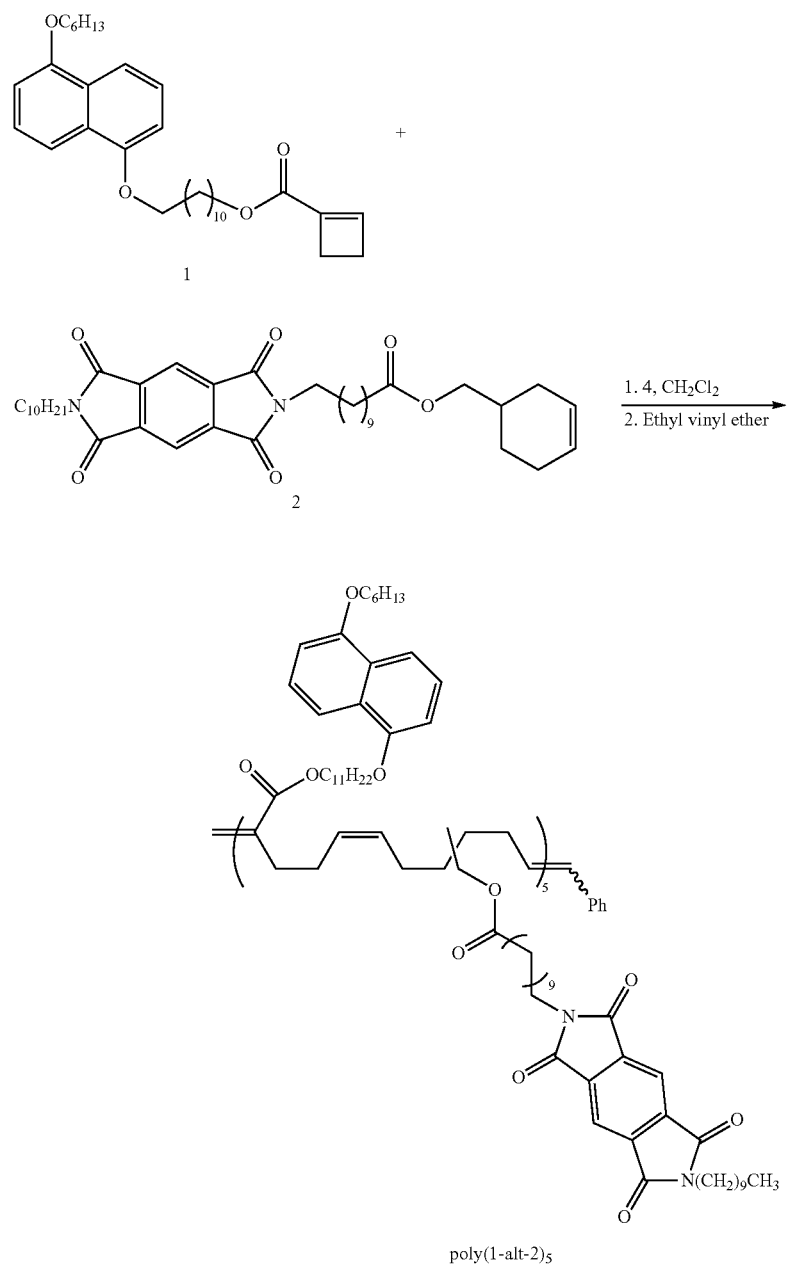
poly(1-alt-2)₅
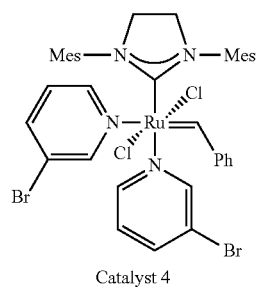
Catalyst 4
Mes = "mesityl", 2,4,6-trimethylphenyl Scheme 2

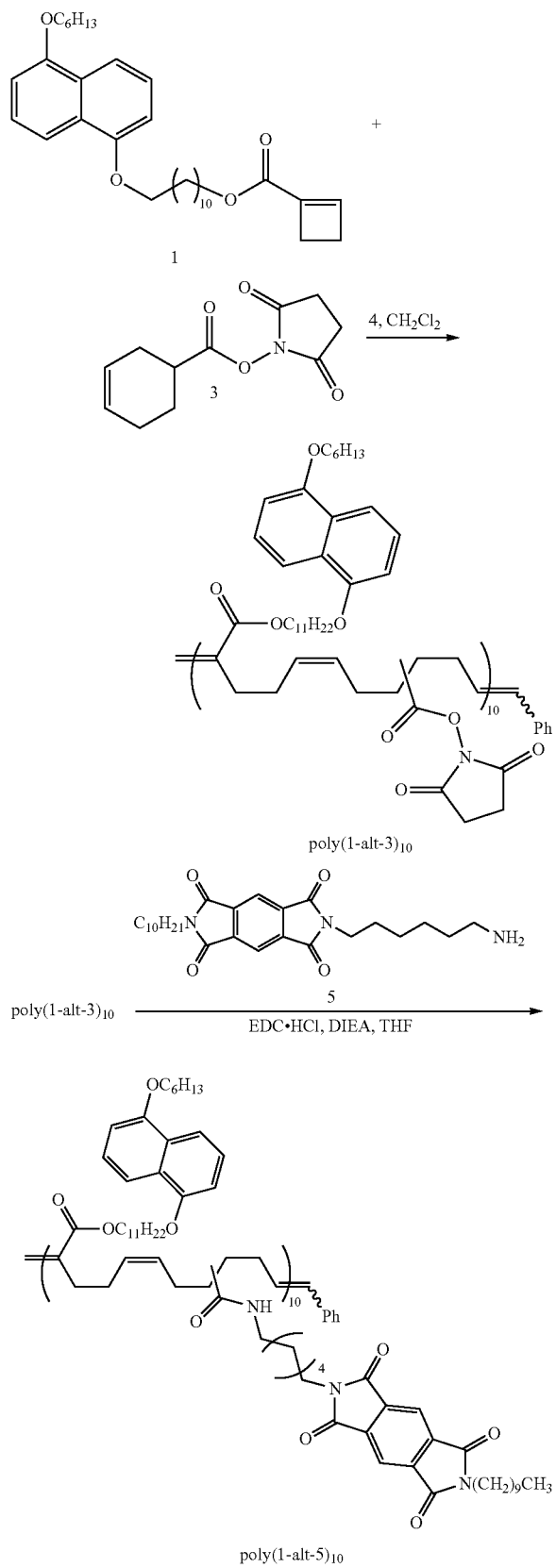

Scheme 3

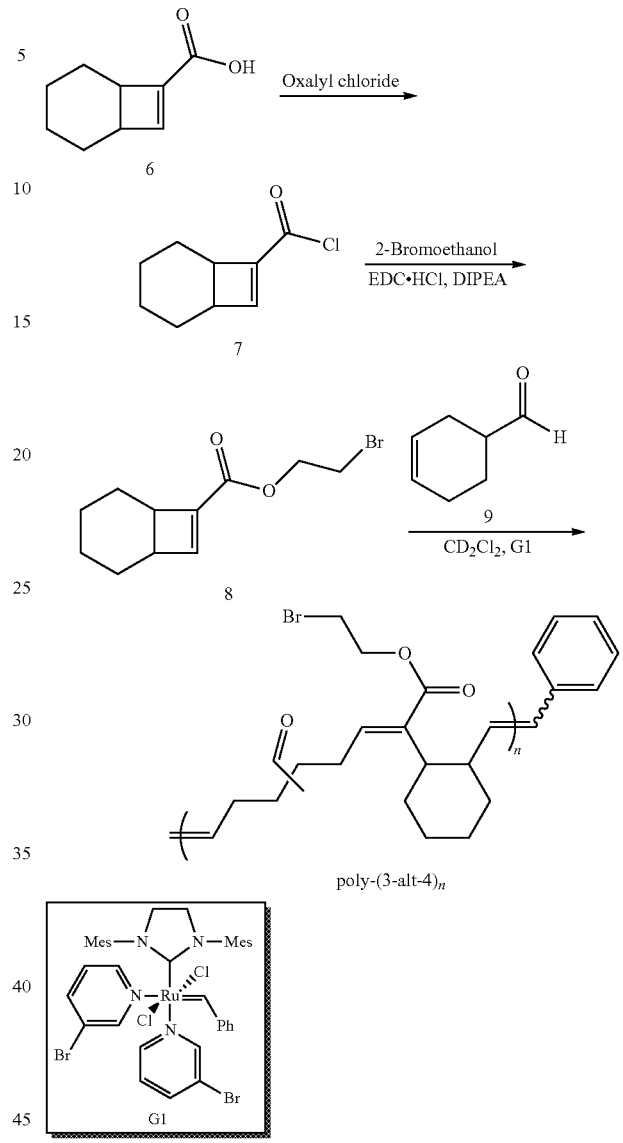

The target monomers and catalyst are shown in FIG. 1. The syntheses of the side-chains are in close analogy to published methods.[4] Based on previous studies,[5] synthetic route 1 (Scheme 1) was first investigated for the alternating copolymerization of the DAN and PDI functionalized CBE and CH monomers, respectively. This route successfully afforded poly(1-alt-2)$_5$. However, longer polymerization times were required due to the significant steric hindrance presented by the side-chain units. This resulted in a decrease in the rate of polymerization inhibiting the formation of higher molecular weight polymers.

To minimize steric hindrance and to achieve a higher degree of polymerization, a revised synthetic route was applied using DAN-CBE 1 and a cyclohexene functionalized with N-hydroxysuccinimide (NHS) (compound 3) for AROMP (Scheme 2). The NHS group is less bulky than the PDI, and is not reactive during the polymerization. The PDI ester can then be formed via a post-polymerization functionalization strategy to generate poly(1-alt-5)$_{10}$. This modified route not only allowed for a higher degree of polymerization, but also provided an alternative strategy for the incorporation of the PDI moiety.

Previous studies on poly(CBE-alt-CH)$_n$ revealed signals in the $^1$H NMR spectrum corresponding to concentration-independent intramolecular backbiting of the enoic ruthenium carbene on the unhindered disubstituted alkenes in the polymer backbone.[5] As a result, polydispersity indices of unfunctionalized poly(CBE-alt-CH)$_n$ were larger than 2 and a significant fraction of the polymer was cyclic. In our case, poly(1-alt-2)$_{10}$ and poly(1-alt-5)$_{10}$ did not show any proton resonance signals due to backbiting, had PDIs lower than 1.3, and displayed a monomodal distribution. We hypothesize that backbiting is inhibited by the increased steric hindrance at the enoic carbene and disubstituted alkene in combination with the restricted flexibility of the polymer backbone upon modification with larger substituents. As a consequence, longer AROMP copolymers were obtained than previously reported.

We designed a new set of cyclobutene derivatives as monomers with bicyclic structures which are very strained and can incorporate rings into the polymeric backbone.[5] Therefore we utilized functional group Br containing bicyclo[4.2.0]oct-7-ene-7-carboxylate and aldehyde containing cyclohexene as the AROMP pair which provides a facile approach to prepare long and completely alternating copolymers with orthogonal functional groups. Post-polymerization modification of Br with an azide group allows click-chemistry while the aldehyde can be coupled to a hydrazide to introduce fluorophores which are not compatible with AROMP reactions.

The alternating copolymers were further modified according to Scheme 4 to crosslink with dansyl hydrazide (DH) and form poly(3'-alt-4-DH)$_n$; it was coupled with Boc-Trp-alkyn to form poly(3'-Trp-alt-4)$_n$; both fluorophores were introduced in a one-pot reaction to provide poly(3'-Trp-alt-4-DH)$_n$.

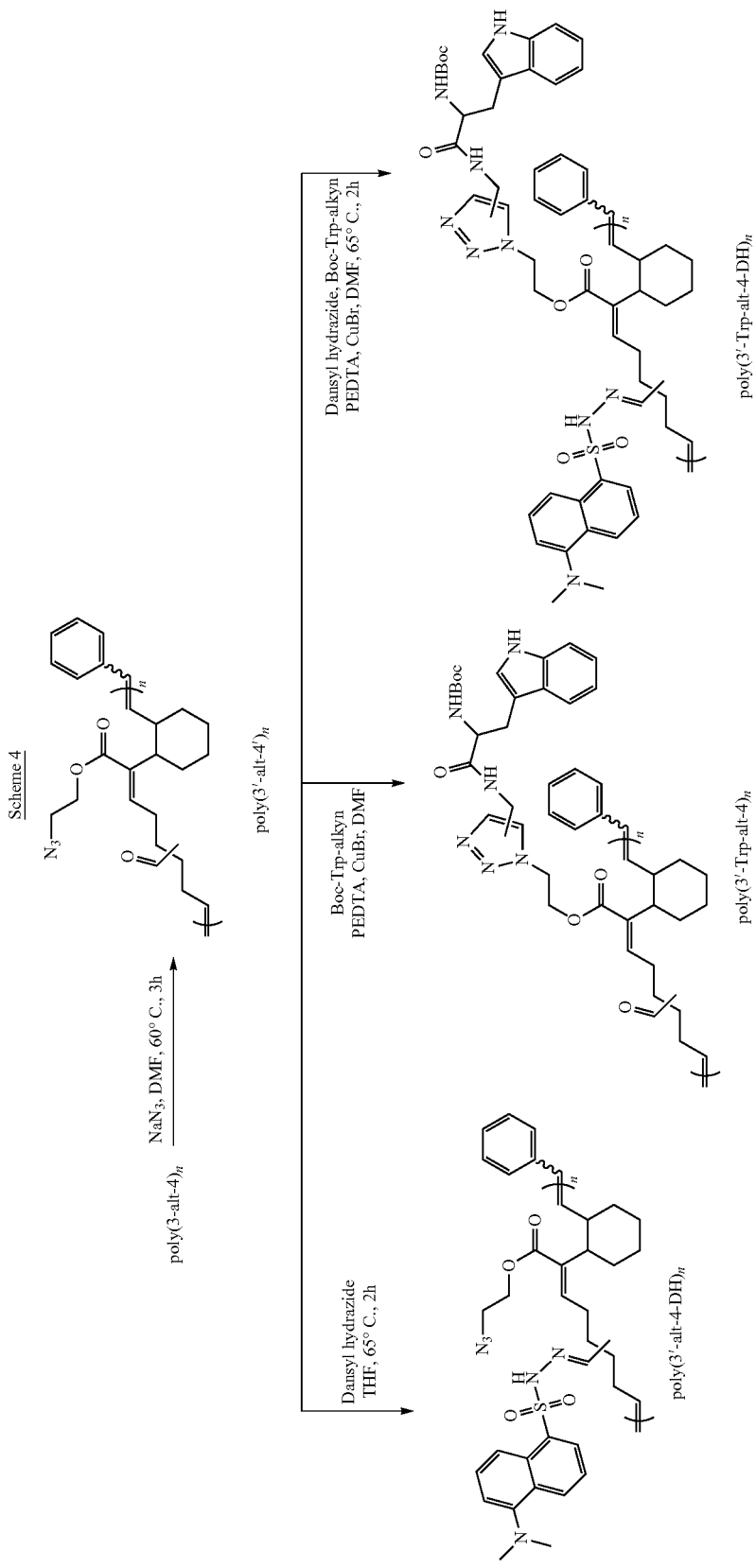

UV-Vis spectroscopy was utilized to investigate the charge-transfer between the side-chains of the alternating copolymers in solution. The UV-Vis spectrum of poly(1-alt-5)$_{10}$ (3 mM in chloroform) shows a charge-transfer absorbance at the characteristic wavelength (FIG. 2a—light blue trace) indicating that the side-chains are able to favorably orient to transfer energy in this system. A concentration study from 3 mM to 100 μM was carried out to determine if these interactions occur inter- or intramolecularly. As shown in FIG. 2a, the charge-transfer absorbance signal was persistent even at low concentrations. Moreover, the absorbance followed Beer-Lambert behavior based on the concentration of polymer (FIG. 2b), which demonstrated that the charge-transfer is intramolecular. Additionally, the aromatic signals in the $^1$H NMR spectrum of poly(1-alt-5)$_{10}$ are shifted upfield in comparison to the individual monomers (Figure S10). These shifts further indicate the pi-pi stacking of the donor-acceptor aromatic units, and are consistent with similar shifts previously reported for partially-folded polymers.[6]

Figure 2:
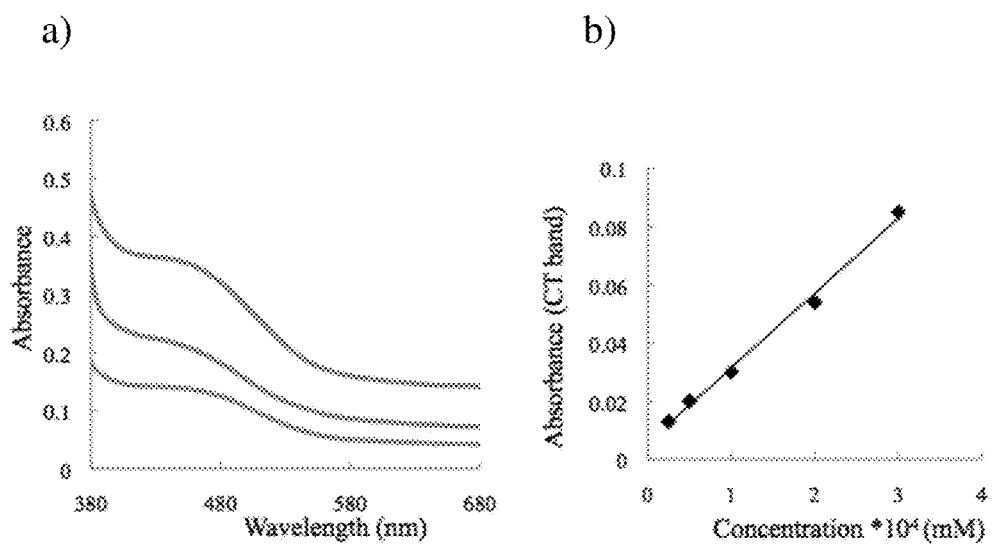
FIG. 2 shows partial UV-Vis spectra of the charge-transfer region in chloroform. a) Comparison of alternating copolymers. Upper trace=3 mM poly(1-alt-5)$_{10}$, middle trace=100 µM poly(1-alt-5)$_{10}$, lower trace=3 mM poly(NB-alt-COE)-block-poly(COE). b) Plot of charge-transfer absorbance versus concentration of poly(1-alt-5)$_{10}$.
Figure 3:
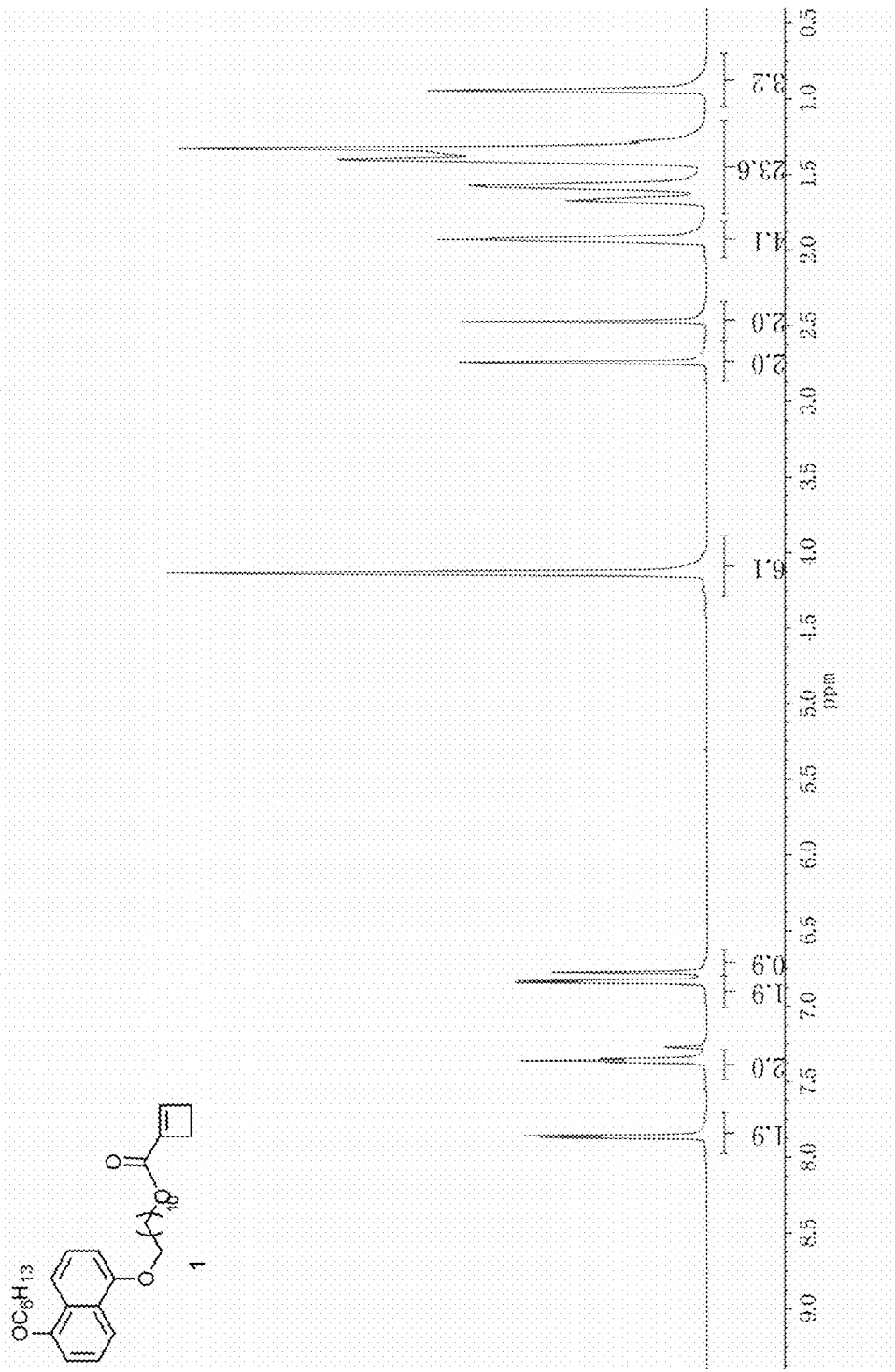
FIG. 3 depicts the $^1$H-NMR spectrum of 11-(5-(hexyloxy)naphthalen-1-yloxy)undecyl cyclobut-1-enecarboxylate (1)
Figure 4:
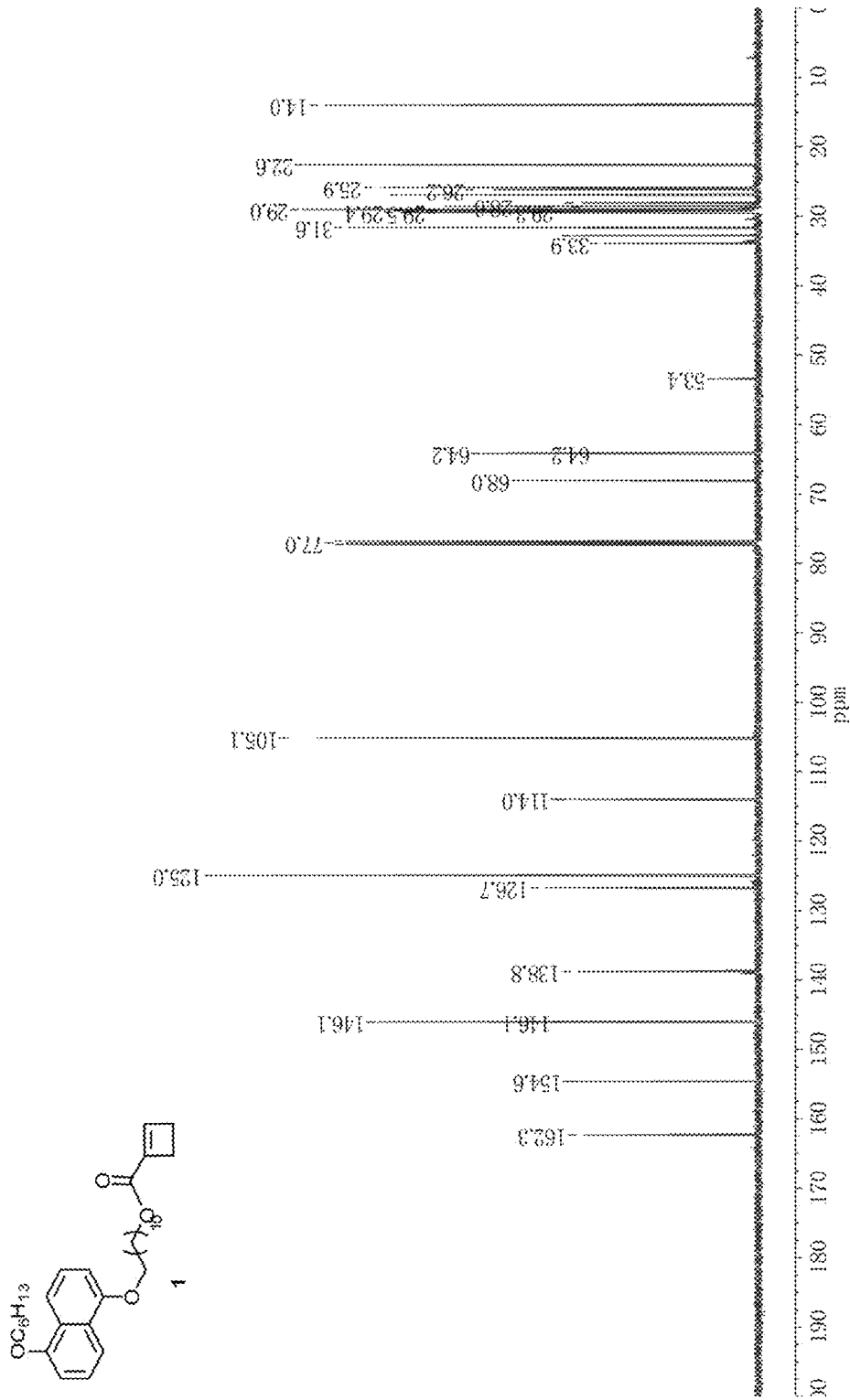
FIG. 4 depicts the $^{13}$C-NMR spectrum of 11-(5-(hexyloxy)naphthalen-1-yloxy)undecyl cyclobut-1-enecarboxylate (1)
Figure 5:
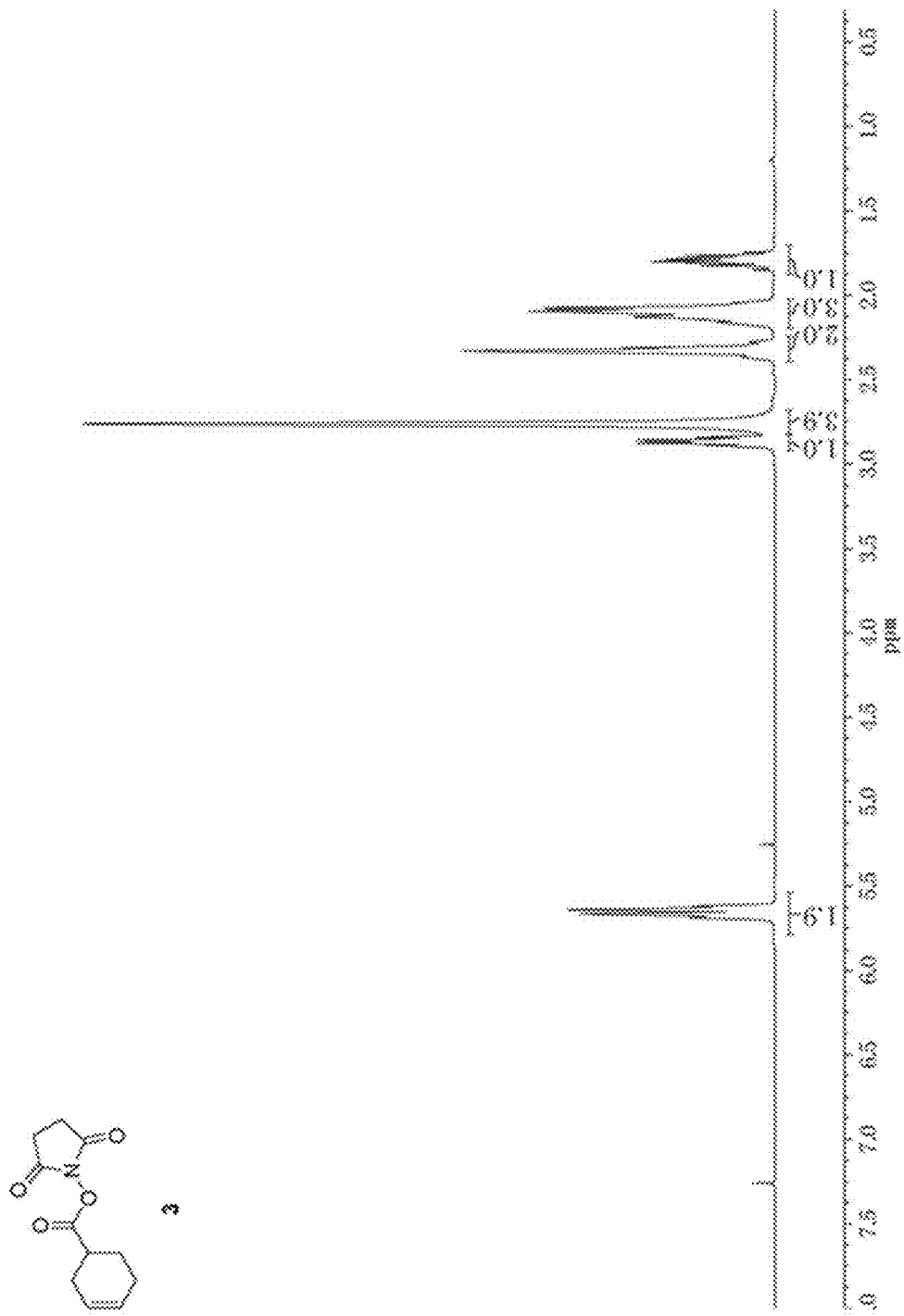
FIG. 5 depicts the $^1$H-NMR spectrum of 2,5-dioxopyrrolidin-1-yl cyclohex-3-enecarboxylate (3).
Figure 6:
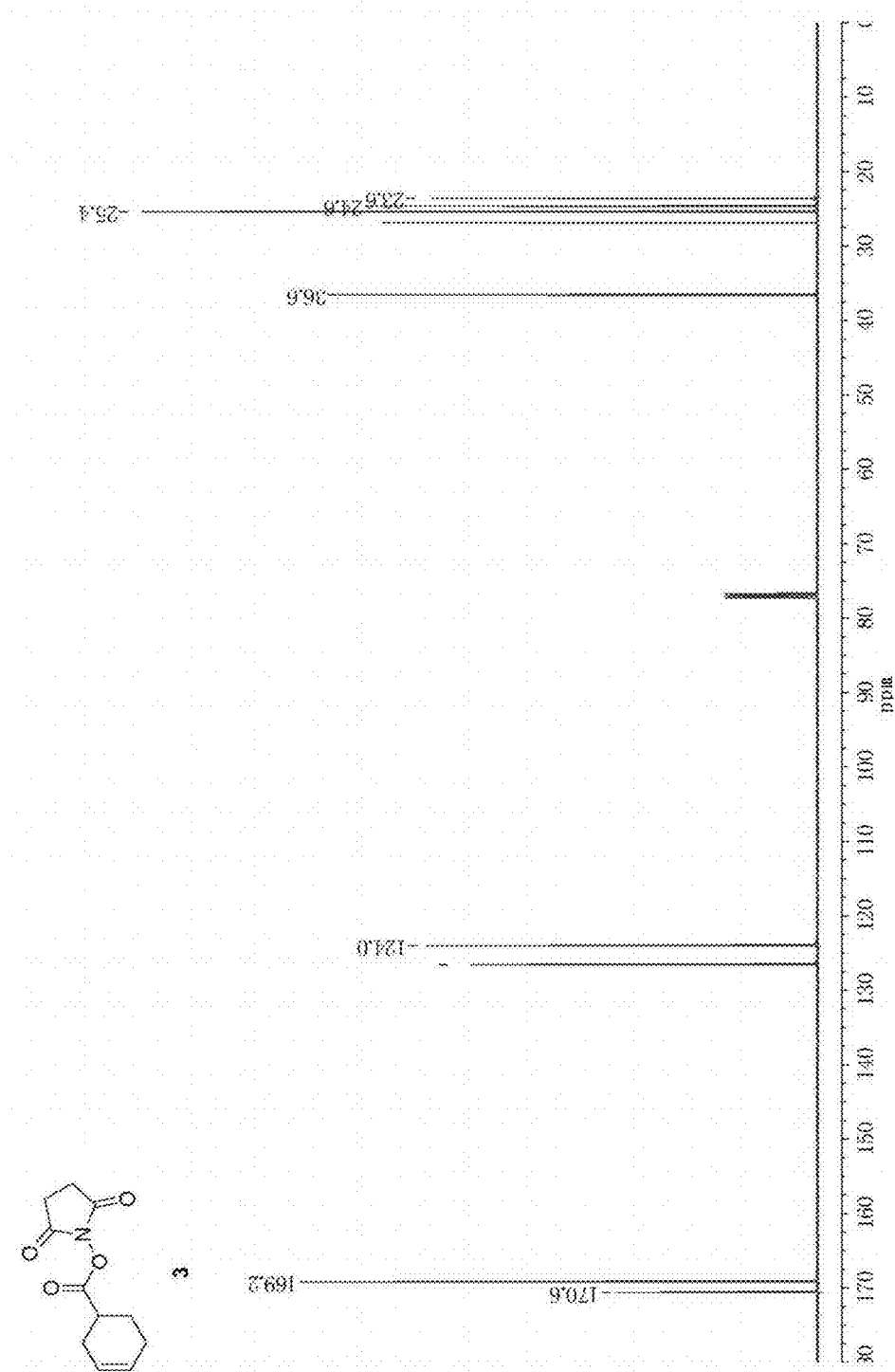
FIG. 6 depicts the $^{13}$C-NMR spectrum of 2,5-dioxopyrrolidin-1-yl cyclohex-3-enecarboxylate (3).
Figure 7:
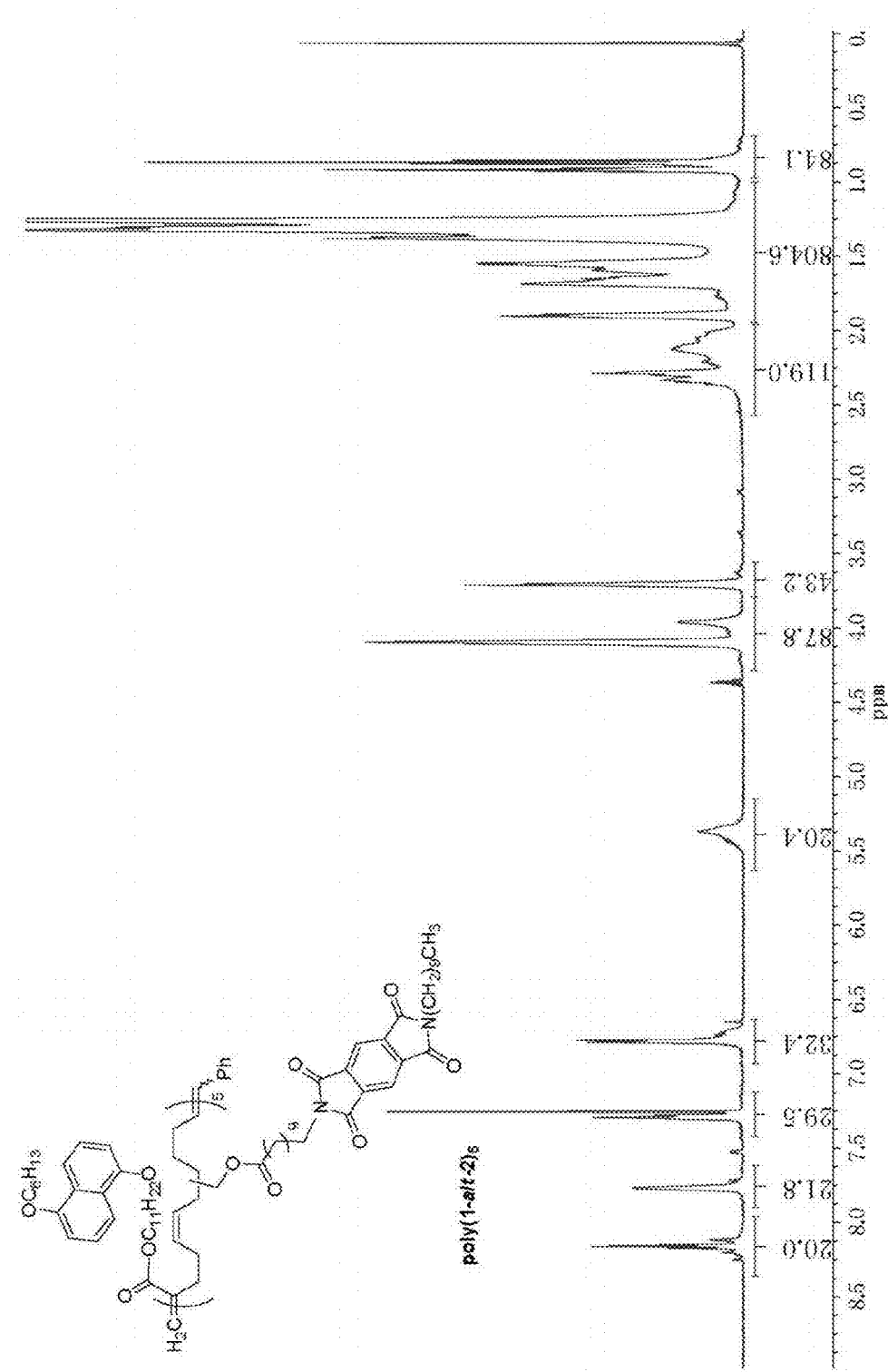
FIG. 7 depicts the $^1$H-NMR spectrum of poly(1-alt-2)$_5$.
Figure 8:
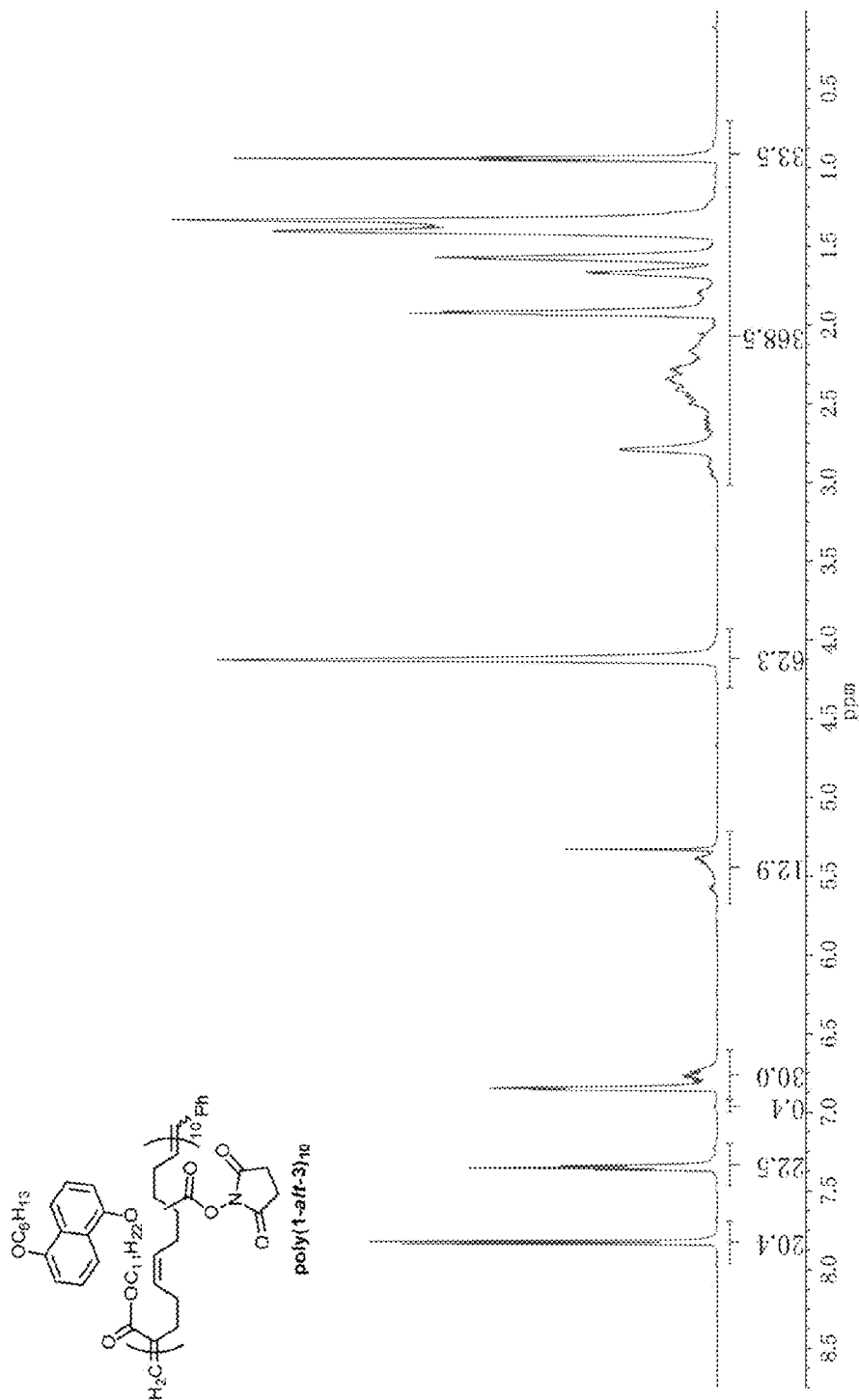
FIG. 8 depicts the $^1$H-NMR spectrum of poly(1-alt-3)$_{10}$.
Figure 9:
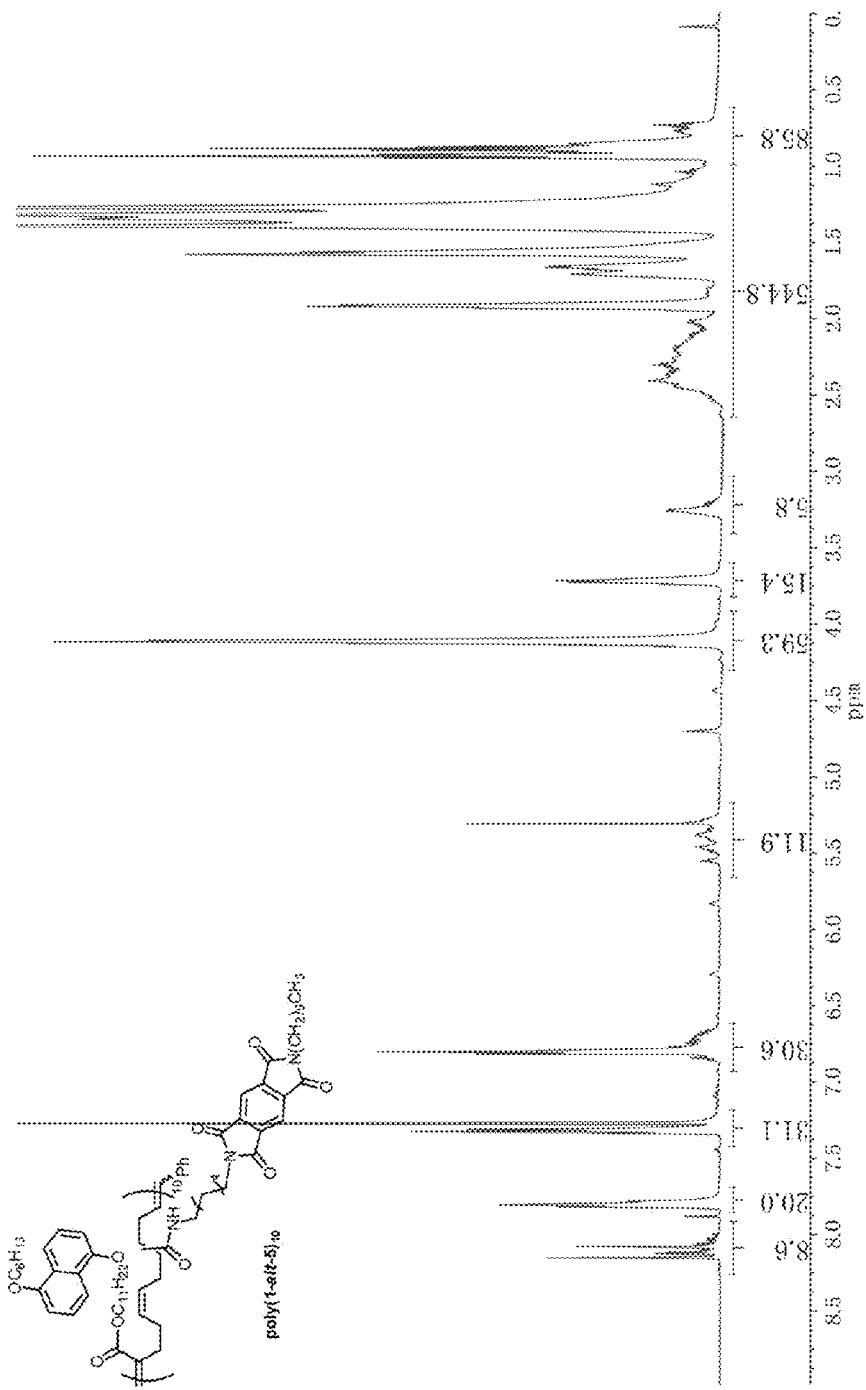
FIG. 9 depicts the $^1$H-NMR spectrum of poly(1-alt-5)$_{10}$.
Figure 10:
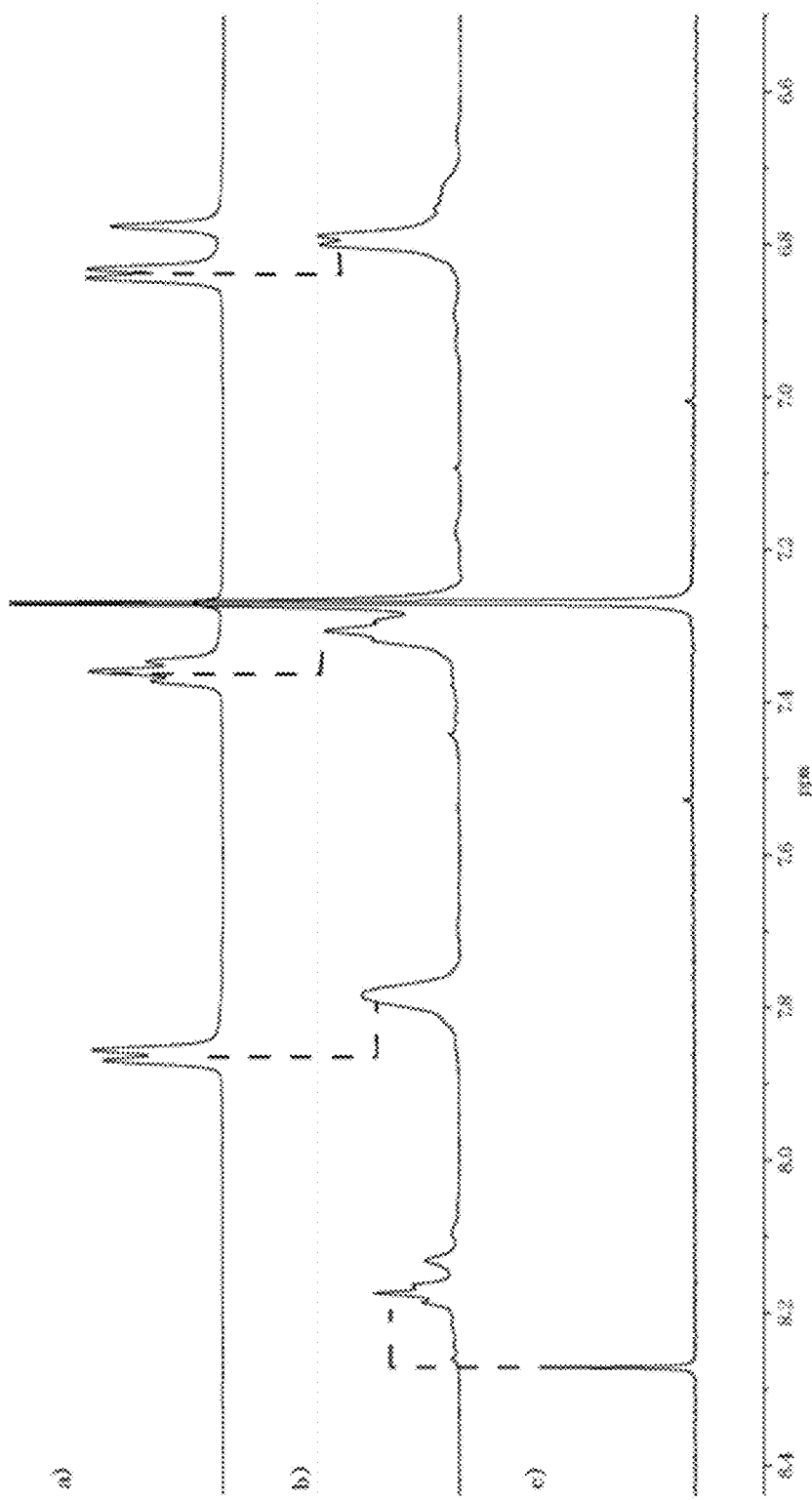
FIG. 10 depicts a partial $^1$H-NMR spectrum of a) 1; b) poly(1-alt-2)$_5$; and c) 2.
Figure 11:
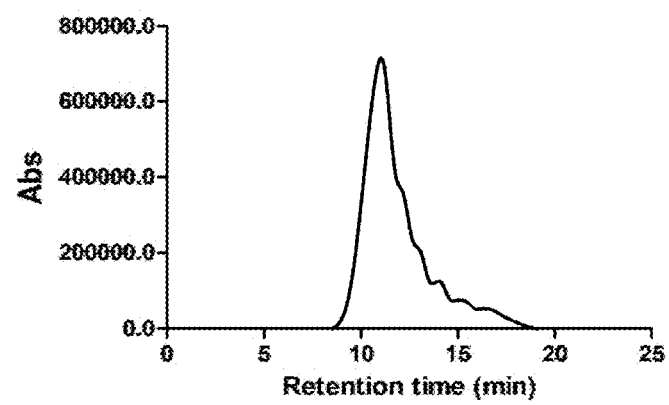
FIG. 11 depicts GPC traces of alternating copolymers. a) poly(1-alt-2)$_5$; b) poly(1-alt-5)$_{10}$. Molecular weights and polydispersity indices were measured using UV detection with CH$_2$Cl$_2$ as the eluent and a flow rate of 0.700 mL/min on an American Polymer Standards column (Phenogel 5µ MXL GPC column, Phenomenex). All GPCs were calibrated using poly(styrene) standards and carried out at 30° C.
Figure 11:
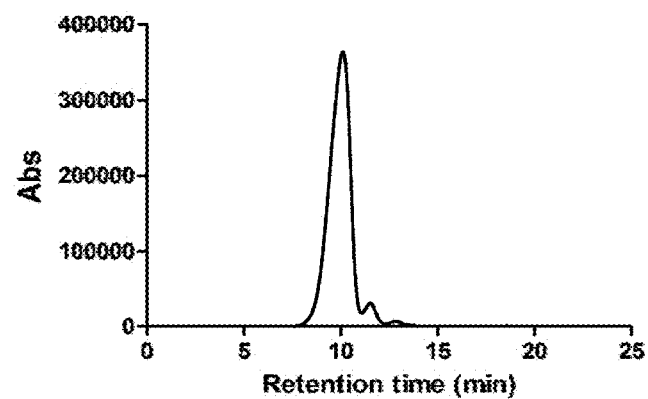
Figure 12:
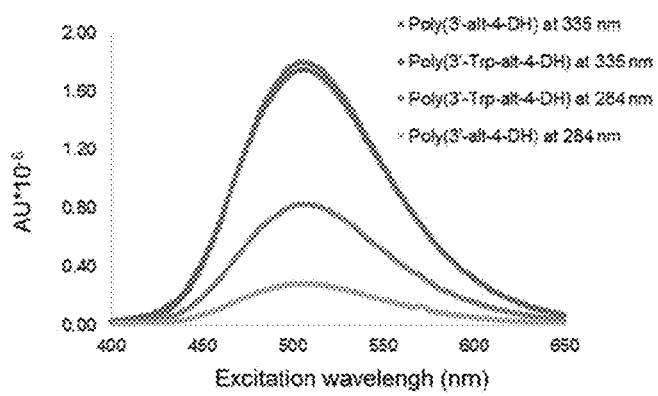
FIG. 12 depicts fluorescence of the polymers. a) The emission spectra of poly(3'-alt-4-DH)$_n$ and poly(3'-Trp-alt-4-DH)$_n$ (1.2 µM in THF) excited at characteristic wavelengths of tryptophan (284 nm) and dansyl fluorophore (335 nm). b) Plot of charge-transfer absorbance of poly(3'-alt-4-DH)$_n$ and poly(3'-Trp-alt-4-DH)$_n$ versus concentration ranging from 0.2 µM and 3 µM. c) Concentration dependence of fluorophores without the backbone showed no emission difference between a two fluorophore mixture and dansyl fluorophore alone.
Figure 12:
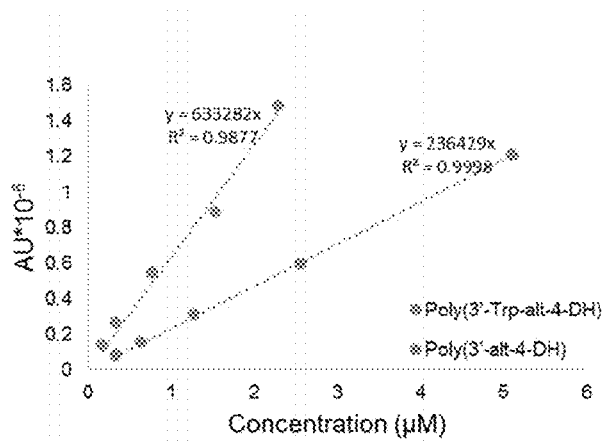
Figure 12:
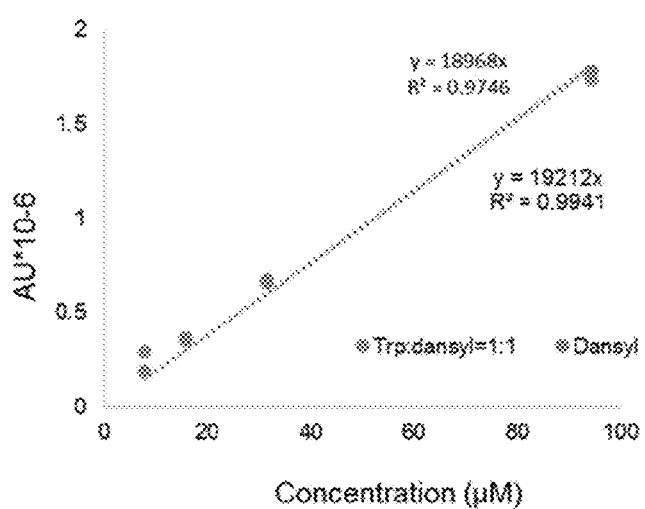

We compared the charge-transfer absorbance of the functionalized poly(CBE-alt-CH)s to the previously reported functionalized poly(NB-alt-COE)-b-COE.[4] As shown in FIG. 2, poly(1-alt-5)$_{10}$ exhibits a higher charge-transfer absorbance intensity in comparison to the NB/COE polymers at the same concentration, which indicates that the new poly(1-alt-5)$_{10}$polymers more favorably align the aromatic units of the donor and acceptor moieties.

In conclusion, we have demonstrated the AROMP of CBE and CH monomers containing bulky DAN/PDI side-chains. We attribute inhibition of backbiting to the steric hindrance provided by bulky side-chains around the carbene and the polymer alkenes. UV-Vis spectroscopic analysis shows a charge-transfer absorbance signal for the perfectly alternating copolymers signifying the alignment of the side-chains. The new polymers demonstrate an enhancement of charge-transfer in comparison to previously studied polymers, indicating that the sequence specificity in alternating CBE-CH copolymers provides efficient energy transfer.

Throughout this application, various publications, reference texts, textbooks, technical manuals, patents, and patent applications have been referred to. The teachings and disclosures of these publications, patents, patent applications and other documents in their entireties are hereby incorporated by reference into this application to more fully describe the state of the art to which the present invention pertains. However, the citation of a reference herein should not be construed as an acknowledgement that such reference is prior art to the present invention.

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way.

EXAMPLES 11-((5-(hexyloxy)naphthalen-1-yl)oxy)undecan-1-ol 11-((5-(hexyloxy)naphthalen-1-yl)oxy)undecan-1-ol was synthesized from 1,5-dihydroxynapthalene, 1-bromohexane, and 11-bromo-1-undecanol in two consecutive steps using a catalytic Williamson ether synthesis.[4]

Cyclobut-1-enecarboxylic Acid

Cyclobut-1-enecarboxylic acid was prepared according to the procedure for the preparation of 3,3-dimethylcylobutene carboxylic acid as described by Campbell et al.[7] and modified as previously reported.[5] $^1$H-NMR (400 MHz, CDCl$_3$) δ 10.23 (bs, 1H), 6.94 (t, J=1.2 Hz, 1H), 2.76 (t, J=3.2 Hz, 2H), 2.51 (td, J=3.2 Hz, 1.2 Hz, 2H). $^{13}$C NMR (100 MHz, CDCl$_3$) δ 167.5, 150.1, 138.4, 29.1, 27.5.

11-(5-(hexyloxy)naphthalen-1-yloxy)undecyl cyclobut-1-enecarboxylate (1)

To a solution of cyclobut-1-enecarboxylic acid (190 mg, 1.94 mmol) and dicyclohexylcarbodiimide (DCC) (417 mg, 2.04 mmol) in CH$_2$Cl$_2$ (10 mL) stirred at 0° C. for 30 minutes, 11-((5-(hexyloxy)naphthalen-1-yl)oxy)undecan-1-ol (400 mg, 0.97 mmol) and a catalytic amount of dimethylaminopyridine (DMAP) were added. The mixture was allowed to warm to rt over 12 h. CH$_2$Cl$_2$ was evaporated under reduced pressure and the crude product was purified by flash chromatography (1:1/hexanes:CH$_2$Cl$_2$) to afford 1 in 35% yield: $^1$H NMR (600 MHz, CDCl$_3$) δ 7.86 (d, J=8.2 Hz, 2H), 7.36 (t, J=7.6 Hz, 2H), 6.84 (d, J=7.2 Hz, 2H), 6.80 (s, 1H), 4.10 (m, 6H), 2.74 (s, 1H), 2.47 (s, 1H), 1.93 (d, J=6.3 Hz, 2H), 1.67 (d, J=6.4 Hz, 1H), 1.58 (d, J=5.7 Hz, 2H), 1.36 (d, J=45.9 Hz, 8H), 0.94 (s, 2H). $^{13}$C NMR (126 MHz, CDCl$_3$) δ 162.3, 154.6, 154.6, 146.1, 146.1, 138.8, 126.7, 124.9, 113.9, 113.9, 105.1, 68.0, 64.2, 64.2, 33.9, 32.7, 31.6, 29.5, 29.4, 29.4, 29.4, 29.3, 29.2, 29.0, 28.7, 28.6, 25.9, 25.8, 22.6, 14.0.

Cyclohex-3-en-1-ylmethyl 3-(6-decyl-1,3,5,7-tetraoxo-6,7-dihydropyrrolo[3,4-f] isoindol-2(1H,3H, 5H)-yl)propanoate (2)

Monomer 2 was prepared from pyromellitic dianhydride and cyclohex-3-en-1-ylmethyl 3-aminopropanoate by methods known in the art.[4]

2,5-dioxopyrrolidin-1-yl cyclohex-3-enecarboxylate (3)

3-Cyclohexene-1-carboxylic acid (100 mg, 0.79 mmol), N-hydroxysuccinimide (100 mg, 0.87 mmol), and ethyl, dimethylaminopropyl carbodiimide hydrochloride (ED-C.HCl) (182 mg, 0.95 mmol) were dissolved in CH$_2$Cl$_2$ and cooled in an ice bath. Then DIEA was added to adjust the pH to 8-9. The reaction was stirred for 16 h and washed with 5% Na$_2$CO$_3$ (50 mL). The organic phase was dried and condensed, followed by flash chromatography, eluted with 100% CH$_2$Cl$_2$ to yield a white solid in 80% yield: $^1$H NMR (600 MHz, CDCl$_3$) δ 5.88-5.44 (m, 2H), 3.01-2.80 (m, 1H), 2.76 (s, 4H), 2.42-2.22 (m, 2H), 2.17-1.92 (m, 3H), 1.90-1.62 (m, 1H). $^{13}$C NMR (100 MHz, CDCl$_3$) δ 170.6, 169.2, 126.6, 124.0, 36.6, 26.9, 25.4, 24.6, 23.6.

2-(6-aminohexyl)-6-decylpyrrolo[3,4-f]isoindole-1, 3,5,7(2H,6H)-tetraone (5)

Compound 5 was synthesized from pyromellitic dianhydride, decylamine, and N-Boc-1,6-hexanediamine according to methods known in the art.[4]

2-Bromoethyl bicyclo[4.2.0]oct-7-ene-7-carboxylate (6)

Bicyclo[4.2.0]alkene carboxylic acid was obtained according to the literature with a yield of 62%.[8,9,21] The acid (500 mg, 3.3 mmol) was dissolved in 5 mL of CH$_2$Cl$_2$ and was cooled in an ice bath when oxalyl chloride (5 mL)

was added. The reaction was stirred for 30 min followed by evaporation to yield bicyclo[4.2.0]oct-7-ene-7-carbonyl chloride as off white oil. 2-Bromoethanol (1.2 mg, 10 mmol), EDC.HCl (630 mg, 3.3 mmol), DIPEA (425 mg, 3.3 mmol) were mixed with the acyl chloride oil in 20 mL of $CH_2Cl_2$. The mixture was stirred for 16 h and was washed with 5% $NaHCO_3$ (3×), 1N HCl (3×) and brine (2×) sequentially and dried over anhydrous $MgSO_4$. The solvent was filtered and removed by evaporation. The crude was subjected to flash silica chromatography (30:70/hexane: $CH_2Cl_2$) to yield 3 (590 mg, 70%): $^1$H NMR (500 MHz, $CD_2Cl_2$): δ 6.91 (d, J=1.1 Hz, 1H), 4.46 (m, 2H), 3.60 (t, J=6.1 Hz, 2H), 3.04 (dd, J=10.3 Hz, J=5.6 Hz, 1H), 2.77 (td, J=5.6 Hz, J=1.1 Hz, 1H), 1.74 (m, 3H), 1.55-1.38 (m, 5H). $^{13}$C NMR (100 MHz, $CDCl_3$) δ 161.4, 151.6, 141.0, 63.0, 40.0, 38.4, 28.6, 23.4, 18.8, 18.2. HRMS (ESI) calcd. for $C_{11}H_{15}BrO_2$ [M+H]$^+$ 258.0255, found 258.0248.

Boc-Trp-OH

Tryptophan (1.00 g, 4.90 mmol) was dissolved in saturated $NaHCO_3$ aqueous solution and cooled in an ice bath. Boc anhydride (2.14 g, 9.80 mmol) was dissolved THF and added dropwise into the tryptophan solution and the reaction was stirred for 10 h. The organic solvent was removed by evaporation and the remaining aqueous solution was washed with $CH_2Cl_2$ (3×20 mL). The water layer was acidified with 1N HCl to pH=2 and was extracted with $CH_2Cl_2$ (3×20 mL). The organic layer was dried over $MgSO_4$. The solvent was filtered and removed by evaporation to yield Boc-Trp-OH as a white solid. It was recrystallized in ethyl acetate with hexane and used without further purification.

Boc-Trp-alkyn

BocTrp-OH (500 mg, 1.64 mmol), propagyl amine (82.1 mg, 1.49 mmol), EDC.HCl (347 mg, 1.80 mmol) and DIPEA (233 mg, 1.80 mmol) were mixed in THF. The reaction was stirred for 10 h and THF was removed by evaporation. The residue was dissolved in $CH_2Cl_2$ and washed sequentially with 5% $NaHCO_3$ (3×), 1N HCl (3×) and brine (2×) and dried over anhydrous $MgSO_4$. The solvent was filtered and removed by evaporation and the crude was subjected to flash silica chromatography (2% MeOH in $CH_2Cl_2$) to yield Boc-Trp-alkyn (390 mg, 78%). $^1$H NMR (700 MHz, $CDCl_3$) δ 8.28 (s, 1H), 7.66 (d, J=7.5 Hz, 1H), 7.38 (d, J=8.1 Hz, 1H), 7.25-7.20 (m, 1H), 7.18-7.13 (m, 1H), 7.06 (s, 1H), 6.12 (s, 1H), 5.18 (s, 1H), 4.48 (s, 1H), 3.93 (s, 2H), 3.32 (s, 1H), 3.21 (s, 1H), 2.17 (s, 1H), 1.44 (s, 9H). $^{13}$C NMR (176 MHz, $CDCl_3$) δ 171.5, 155.5, 136.2, 127.5, 123.3, 122.3, 119.8, 118.8, 111.3, 110.4, 80.3 79.16, 71.5, 55.0, 29.1, 28.3. ESI (M/Z) [M+H]$^+$ 341.2.

General Procedure for AROMP

The NMR tube was evacuated under high vacuum for 15 min, and then was purged with $N_2$ gas for another 15 min. Under an $N_2$ atmosphere, a solution of monomer A in $CD_2Cl_2$ (300 µL) was added to the NMR tube. Then a solution of catalyst $(H_2IMes)(3-Br-Py)_2(Cl)_2Ru=CHPh$ in $CD_2Cl_2$ (300 µL) was added to the NMR tube. After complete mixing of the solution, the NMR tube was spun for 60 min at an elevated temperature 37° C. until the precatalyst had reacted as can be observed by disappearance of ruthenium alkylidene proton at 19 ppm. Monomer B (cyclohexene derivative) in $CD_2Cl_2$ (100 µL) was added to the NMR tube. The reaction was quenched in 8 h with ethyl vinyl ether (50 µL) and the resulting solution was stirred for another 1 h.

Poly(1-alt-2)$_5$

The reaction was monitored by $^1$H NMR. The NMR tube was evacuated under high vacuum for 15 min, and then was purged with $N_2$ gas for another 15 min. Under an $N_2$ atmosphere, a solution of monomer 1 (29.6 mg, 0.060 mmol) in $CD_2Cl_2$ (300 µL) was added to the NMR tube. Then a solution of catalyst $(H_2IMes)(3-Br-Py)_2(Cl)_2Ru=CHPh$ (4, 5.3 mg, 6.0 µmol) in $CD_2Cl_2$ (300 µL) was added to the NMR tube. After complete mixing of the solution, the NMR tube was spun for 60 min at an elevated temperature 37° C. until the precatalyst had reacted as can be observed by disappearance of ruthenium alkylidene proton at 19 ppm. Monomer 2 (19.5 mg, 0.030 mmol) in $CD_2Cl_2$ (100 µL) was added to the NMR tube. The reaction was quenched in 8 h with ethyl vinyl ether (50 µL) and the resulting solution was stirred for another 1 h. The mixture was condensed to give a dark brown oil which was further purified by column chromatography (100:1/$CH_2Cl_2$: MeOH (methanol)) to yield an orange solid in 55% yield. $^1$H NMR (600 MHz, $CDCl_3$) δ 8.26-7.92 (m, 8H), 7.83-7.74 (m, 10H), 7.42-7.20 (m, 10H), 6.93-6.62 (m, 15H), 5.66-5.17 (m, 8H), 4.30-3.91 (m, 41H), 3.72 (m, 16H), 3.41-3.03 (m, 6H), 2.65-1.02 (m, 382H), 0.99-0.62 (m, 34H). Mn$^{cal}$=5748, Mn$^{GPC}$=3291, Mw$^{GPC}$=4252, PDI=1.29.

Poly(1-alt-5)$_{10}$

The reaction was monitored by $^1$H NMR. The NMR tube was evacuated under high vacuum for 15 min, and then was purged with $N_2$ gas for another 15 min. Under an $N_2$ atmosphere, a solution of monomer 1 (29.6 mg, 0.060 mmol) in $CD_2Cl_2$ (300 µL) was added to the NMR tube. Then a solution of catalyst $(H_2IMes)(3-Br-Py)_2(Cl)_2Ru=CHPh$ (4, 5.3 mg, 6.0 µmol) in $CD_2Cl_2$ (300 µL) was added to the NMR tube. After complete mixing of the solution, the NMR tube was spun for 60 min at 25° C. until the precatalyst had reacted as can be observed by disappearance of ruthenium alkylidene proton at 19 ppm. Monomer 3 (26.8 mg, 0.120 mmol) in $CD_2Cl_2$ (100 µL) was added to the NMR tube. The reaction was quenched in 6 h with ethyl vinyl ether (50 µL) and the resulting solution was stirred for another 1 h. The mixture was condensed to give a dark brown oil which was further purified by column chromatography (100:1/$CH_2Cl_2$:MeOH) to yield an orange solid in 75% yield. $^1$H NMR (600 MHz, $CDCl_3$) δ 7.84 (m, 20H), 7.32 (m, 20H), 6.98-6.56 (m, 30H), 5.33 (m, 13H), 4.11 (s, 3H), 292-1.25 (m, 366H), 0.95 (m, 30H). The resulting polymer poly(1-alt-3)$_{10}$ (27.2 mg, 3.7 µmol) was dissolved in dry THF and cooled in an ice bath. EDC.HCl (7.1 mg, 37 µmol), DIEA (9.7 mg, 74 µmol), and 2-(6-aminohexyl)-6-decylpyrrolo[3,4-f]isoindole-1,3,5,7(2H,6H)-tetraone (5) (34 mg, 74 µmol) were added. The mixture was stirred for 2 days and then filtered, followed by column chromatography (5:95/acetone/$CH_2Cl_2$) to yield an orange solid in 20% yield. $^1$H NMR (600 MHz, $CDCl_3$) δ 8.26-7.92 (m, 9H), 7.80 (dd, J=14.4, 6.1 Hz, 20H), 7.42-7.18 (m, 20H), 6.93-6.62 (m, 30H), 5.66-5.17 (m, 12H), 4.30-3.91 (m, 59H), 3.72 (dd, J=14.7, 7.1 Hz, 15H), 3.41-3.03 (m, 6H), 2.65-0.99 (m, 545H), 0.99-0.62 (m, 86H). Mn$^{Cal}$=10948, Mn$^{GPC}$=7966, Mw$^{GPC}$=10221, PDI=1.28.

Poly(3-alt-4)$_n$

Under an $N_2$ atmosphere, 6 (61.8 mg, 0.24 mmol) and G1 (5.3 mg, 0.006 mmol) were mixed in $CD_2Cl_2$ (600 µL) in an NMR tube. NMR spectra were acquired at 25° C. until the G1 had completely reacted as determined by the disappearance of its alkylidene α proton signal. Cyclohex-3-enecarbaldehyde 9 (52.7 mg, 0.48 mmol) was added to the NMR tube. When no further propagation occurred, the reaction was quenched with ethyl vinyl ether and stirred for 30 min. The solvent was evaporated, and the alternating copolymer was purified by chromatography on silica gel (97:3/$CH_2Cl_2$: acetone). $^1$H NMR (500 MHz, $CD_2Cl_2$): δ 9.59 (m, 27H), 7.25 (m, 5H), 6.59 (m, 27H), 5.83 (m, 27H), 5.36 (m, 27H), 4.39 (m, 54H), 3.59 (m, 54H), 3.0-1.25 (m, 560H). $M_n^{calc}$=9700, $M_n^{GPC}$=14823, $M_w^{GPC}$=31649, $Đ_M$=2.13.

Post-polymerization Modification

In the first step of post-polymerization modifications the bromide was converted to an azide by mixing poly(3-alt-4)$_n$ and $NaN_3$ in DMF at 60° C. for 3 hours. Poly(3'-alt-4)$_n$ was obtained after workup. $^1$H NMR of poly(3'-alt-4)$_n$ showed no significant difference from that of poly(3-alt-4)$_n$, so were the GPC traces. Therefore, we obtained IR spectra which showed a distinctive $N_3$ vibration signal at around 2200 $cm^{-1}$.

Poly(3'-alt-4)$_n$

To a solution of poly(3-alt-4)$_n$ (44.0 mg, 4.51 μmol) in anhydrous DMF (1 mL) was added $NaN_3$ (23.0 mg, 353 μmol). The mixture was stirred at 60° C. for 3 h, and water (5 mL) was added and the mixture was extracted with $CH_2Cl_2$ (3×5 mL). The combined organic layers were washed with water and dried over $MgSO_4$. After filtration, the solvent was evaporated by vacuum to give a yellow oil (31.0 mg, 80%). $^1$H NMR (500 MHz, $CD_3OD$): δ 9.50 (m, 27H), 7.24 (m, 5H), 6.48 (m, 27H), 5.78 (m, 27H), 5.30 (m, 27H), 4.20 (m, 59H), 3.50 (m, 59H), 3.00-1.35 (m, 863H). IR (KBr): 3418, 2924, 2854, 2718, 2104, 1716, 1633 $cm^{-1}$.

Poly(3'-alt-4-DH)$_n$

Poly(3'-alt-4) (4.7 mg, 0.54 μmol) and dansyl hydrazide (5.5 mg, 21 μmol) were dissolved in THF (2 mL). The mixture was stirred at 65° C. for 2 h and the solution was concentrated under vacuum. The residue was purified by LH-20 with eluting solvent as THF. $^1$H NMR (400 MHz, $CD_2Cl_2$): δ 8.56 (bs, 47H), 8.42 (bs, 39H), 8.28 (bs, 39H), 8.00 (bs, 47H), 7.54 (bs, 87H), 7.20 (bs, 96H), 6.43 (bs, 27H), 5.68 (bs, 29H), 5.13 (bs, 31H), 4.30 (bs, 137H), 3.46 (bs, 131H), 2.94 (bs, 155H), 2.88 (bs, 243H), 2.86 (s, 172H), 2.80-1.01 (m, 1618H). $M_n^{calc}$=16369, $M_n^{GPC}$=19325, $M_w^{GPC}$=34382, $Đ_M$=1.78.

Poly(3'-Trp-alt-4)$_n$

Under an $N_2$ atmosphere, poly(3'-alt-4)$_n$. (5.9 mg, 0.67 μmol), Boc-Trp-alkyn (10.6 mg, 25.6 μmol), CuBr (1.7 mg, 0.20 μmol) and PEDTA (6.7 μL) were mixed in THF (1 mL). After stirring for 12 h, the solution was concentrated and the residue was purified by LH-20 with eluting solvent as THF. $M_n^{calc}$=16715, $M_n^{GPC}$=12472, $M_w^{GPC}$=20226, $Đ_M$=1.62.

Poly(3'-Trp-alt-4-DH)$_n$

Under an $N_2$ atmosphere, poly(3'-alt-4)$_n$(7.0 mg, 0.80 mmol), dansyl hydrazide (8.2 mg, 31 μmol), Boc-Trp-alkyn (12.5 mg, 30.0 mmol), CuBr (2.0 mg, 0.24 mmol) and PEDTA (7.9 μL) were mixed in THF (1 mL). The mixture was stirred at 65° C. for 12 h, the solution was concentrated and the residue was purified by LH-20 with eluting solvent as THF. $M_n^{calc}$=22491, $M_n^{GPC}$=21645, $M_w^{GPC}$=38312, $Đ_M$=1.747. IR (KBr): 3413, 2929, 2854, 1707, 1690 $cm^{-1}$.

(1) Hawker, C. J.; Bosman, A. W.; Harth, E. *Chemical Reviews* 2001, "New polymer synthesis by nitroxide mediated living radical polymerizations," 101, 3661-3688.

(2) Matyjaszewski, K.; Xia, J. H. *Chemical Reviews* 2001, "Atom transfer radical polymerization," 101, 2921-2990.

(3) Choi, T. L.; Rutenberg, I. M.; Grubbs, R. H. *Angewandte Chemie-International Edition* 2002, "Synthesis of A,B-alternating copolymers by ring-opening-insertion-metathesis polymerization," 41, 3839-3841.

(4) Romulus, J.; Patel, S.; Weck, M. *Macromolecules* 2011, "Facile Synthesis of Flexible, DonorAcceptor Side-Chain Functionalized Copolymers via Ring-Opening Metathesis Polymerization," 45, 70-77. 10.1021/ma201812x (5) Song, A.; Parker, K. A.; Sampson, N. S. *J. Am. Chem. Soc.* 2009, "Synthesis of Copolymers by Alternating ROMP (AROMP)," 131, 3444-3445. 10.1021/ja809661k (6) Lokey, R. S.; Iverson, B. L. *Nature* 1995, "Synthetic molecules that fold into a pleated secondary structure in solution," 375, 303-305.

(7) Campbell, A.; Rydon, H. N. *J. Chem. Soc.* 1953, "596. The synthesis of caryophyllenic acid," 0, 3002-3008.

(8) Tan, L., Parker, K. A., and Sampson, N. S. (2014) A Bicyclo[4.2.0]octene-derived Monomer Provides Completely Linear Alternating Copolymers via Alternating Ring-Opening Metathesis Polymerization (AROMP). *Macromolecules*.

(9) Tan, L., Parker, K. A., and Sampson, N. S. (2014) Tandem Generation of Tetrasubstituted α,β-Unsaturated Amides and Alternating Copolymers via Alternating Ring-Opening Metathesis Polymerization (AROMP).

(10) Song, A., Lee, J., Parker, K. A., and Sampson, N. S. (2010) Scope of the Ring-Opening Metathesis Polymerization (ROMP) Reaction of 1-Substituted Cyclobutenes, *J. Am. Chem. Soc.* 132, 10513-10520.

(11) Tan, L., Parker, K. A., and Sampson, N. S. (2013) A Bicyclo[4.2.0]octene-derived Monomer Provides Completely Linear Alternating Copolymers via Alternating Ring-Opening Metathesis Polymerization (AROMP). *Macromolecules*.

(12) (1999) *Why FRET over genomics?*, Vol. 1.

(13) Rankin, D. A., Schanz, H.-J., and Lowe, A. B. (2007) Effect of the Halide Counterion in the ROMP of exo-Benzyl-[2-(3,5-dioxo-10-oxa-4-aza-tricyclo[5.2.1.02,6] dec-8-en-4-yl)ethyl]dimethyl ammonium Bromide/Chloride, *Macromol. Chem. Phys.* 208, 2389-2395.

(14) Buchowicz, W., Holerca, M. N., and Percec, V. (2001) Self-Inhibition of Propagating Carbenes in ROMP of 7-Oxa-bicyclo[2.2.1]hept-2-ene-5,6-dicarboxylic Acid Dendritic Diesters Initiated with Ru(CHPh)Cl2(PCy3)(1,3-dimesityl-4,5-dihydroimidazol-2-ylidene), *Macromolecules* 34, 3842-3848.

(15) Haigh, D. M., Kenwright, A. M., and Khosravi, E. (2005) Nature of the Propagating Species in Ring-Opening Metathesis Polymerizations of Oxygen-Containing Monomers Using Well-Defined Ruthenium Initiators, *Macromolecules* 38, 7571-7579.

(16) Johnson, J. A., Lu, Y. Y., Burts, A. O., Lim, Y.-H., Finn, M. G., Koberstein, J. T., Turro, N. J., Tirrell, D. A., and Grubbs, R. H. (2010) Core-Clickable PEG-Branch-Azide Bivalent-Bottle-Brush Polymers by ROMP: Grafting-Through and Clicking-To, *J. Am. Chem. Soc.* 133, 559-566.

(17) Boren, B. C., Narayan, S., Rasmussen, L. K., Zhang, L., Zhao, H., Lin, Z., Jia, G., and Fokin, V. V. (2008) Ruthenium-Catalyzed Azide-Alkyne Cycloaddition: Scope and Mechanism, *J. Am. Chem. Soc.* 130, 8923-8930.
(18) Brummelhuis, N., and Weck, M. (2012) Orthogonal Multifunctionalization of Random and Alternating Copolymers, *ACS Macro. Lett.* 1, 1216-1218.
(19) Yang, S. K., and Weck, M. (2007) Modular Covalent Multifunctionalization of Copolymers, *Macromolecules* 41, 346-351.
(20) Love, J. A., Morgan, J. P., Trnka, T. M., and Grubbs, R. H. (2002) A practical and highly active ruthenium-based catalyst that effects the cross metathesis of acrylonitrile, *Angew. Chem. Int. Ed.* 41, 4035-4037.
(21) Snider, B. B., Rodini, D. J., Cionn, R. S. E., and Sealfon, S. (1979) Lewis Acid Catalyzed Reactions of Methyl Propiolate with Unactivated Alkenes, *J. Am. Chem. Soc.* 101, 5283-5493.

We claim:

1. A polymer comprising the repeating unit (Ib) or (Ic):

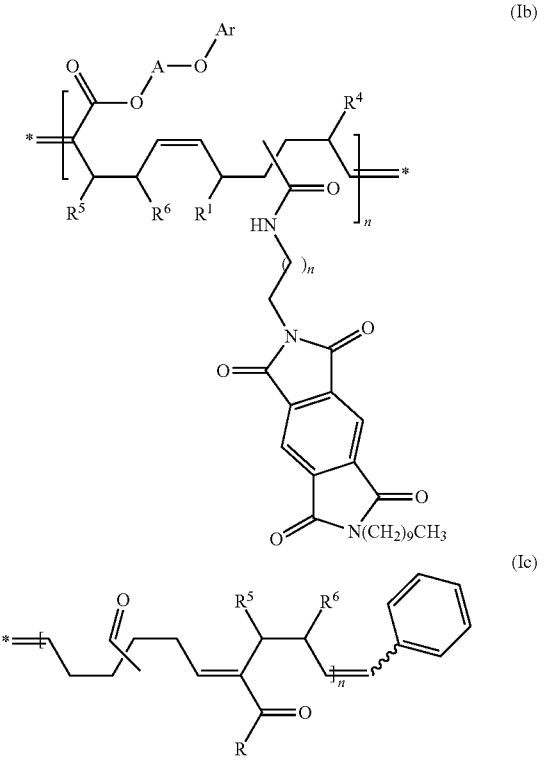

wherein R is selected from the group consisting of H, $C_1$-$C_{20}$ alkyl, $C_2$-$C_{20}$ alkenyl, $C_3$-$C_8$ cycloalkyl, heterocyclyl, aryl, $C_1$-$C_{20}$ alkoxy, $C_1$-$C_{20}$ alkenyloxy, $C_3$-$C_6$ cycloalkyloxy, aryloxy, heterocyclyloxy, $C_1$-$C_{20}$ alkylamino, $C_1$-$C_{20}$ alkenylamino, $C_3$-$C_8$ cycloalkylamino, heterocyclylamino, or arylamino and may be optionally substituted with up to three substituents selected from halo, CN, $NO_2$, oxo, alkyl, cycloalkyl, alkenyl, alkynyl, aralkyl, aryl, and a heterocyclic group;

n is a number between 2 and 20;

$R^1$ through $R^6$ are independently selected from the group consisting of H, aldehyde, $C_1$-$C_{20}$ alkyl, $C_2$-$C_{20}$ alkenyl, $C_3$-$C_6$ cycloalkyl, aryl, heterocyclyl, $C_1$-$C_{20}$ alkoxy, $C_1$-$C_{20}$ acyloxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, arylamino, or halogen;

$R^1$ through $R^6$ may be taken together to form a 5- to 7-membered ring which may be optionally substituted with up to three substituents selected from halo, CN, $NO_2$, oxo, alkyl, cycloalkyl, alkenyl, alkynyl, aralkyl, aryl, or a heterocyclic group;

A is a $C_2$-$C_{20}$ alkyl;

with the proviso that any carbon-carbon double bonds in R or in $R^1$ through $R^6$ are essentially unreactive toward metathesis reactions with the catalyst.

2. The polymer of claim 1, wherein the polymer comprising the repeating unit (Ib) or (Ic) is a cyclic polymer.

3. The polymer of claim 1, wherein polymer comprising the repeating unit (Ib) or (Ic) is a block in a block copolymer.

4. A method of inhibiting microbial growth or inhibiting biofilm formation on a surface comprising the step of contacting one or more microbes with a polymer of claim 1.

5. A method of preparing a therapeutic agent for delivery to a subject comprising combining the therapeutic agent with a polymer of claim 1.

6. The method of claim 5, wherein the therapeutic agent is conjugated to the polymer.

7. The method of claim 5, wherein the therapeutic agent is contained in a micelle comprising the polymer.

* * * * *